(12) United States Patent
Lee

(10) Patent No.: US 8,707,788 B2
(45) Date of Patent: Apr. 29, 2014

(54) SOUND WAVE TESTING DEVICE AND METHOD FOR TESTING SOLAR PANEL

(76) Inventor: Kun Ta Lee, Taipei Hsien (TW)

( * ) Notice: Subject to any disclaimer, the term of this patent is extended or adjusted under 35 U.S.C. 154(b) by 160 days.

(21) Appl. No.: 13/283,680

(22) Filed: Oct. 28, 2011

(65) Prior Publication Data

US 2013/0042689 A1    Feb. 21, 2013

(30) Foreign Application Priority Data

Aug. 19, 2011   (TW) .............................. 100129869 A

(51) Int. Cl.
*G01N 29/04* (2006.01)

(52) U.S. Cl.
USPC .................................. 73/627; 73/588; 73/632

(58) Field of Classification Search
USPC ........................................... 73/627, 588, 632
See application file for complete search history.

(56) References Cited

U.S. PATENT DOCUMENTS

| | | | |
|---|---|---|---|
| 4,366,713 A * | 1/1983 | Gilmore et al. ................. | 73/618 |
| 4,584,879 A * | 4/1986 | Webster et al. ................. | 73/588 |
| 6,167,298 A * | 12/2000 | Levin ............................. | 600/545 |
| 7,884,727 B2 * | 2/2011 | Tran ............................ | 340/573.1 |
| 8,190,385 B2 * | 5/2012 | Rowe et al. ..................... | 702/64 |

FOREIGN PATENT DOCUMENTS

| | | | |
|---|---|---|---|
| JP | 2004019818 | * | 1/2004 |
| TW | 201040519 | | 11/2010 |

OTHER PUBLICATIONS

Taiwan Office Action dated Nov. 27, 2013.
English translation of abstract of TW 201040519 (published Nov. 16, 2010).
English translation (by machine) of Taiwan Office Action dated Nov. 27, 2013.

* cited by examiner

*Primary Examiner* — J M Saint Surin
(74) *Attorney, Agent, or Firm* — McClure, Qualey & Rodack, LLP

(57) ABSTRACT

A sound wave testing device is provided. The sound wave testing device comprises at least one sound output unit for providing at least one first sound signal, at least one sound-collecting element disposed above the at least one sound output unit, at least one sound-receiving unit disposed at one end of the at least one sound-collecting element, and an isolating element disposed between the at least one sound output unit and the at least one sound-collecting element, in which the solar panel is disposed on the isolating element. The at least one first sound signal is transformed into at least one second sound signal while passing through the solar panel. The at least one second sound signal is received and transmitted to at least one sound-receiving unit, and the at least one second sound signal is transformed into at least one digital signal for output.

11 Claims, 8 Drawing Sheets

SOUND WAVE TESTING DEVICE AND METHOD FOR TESTING SOLAR PANEL

This application claims priority to Taiwan Patent Application No. 100129869 filed on Aug. 19, 2011, the disclosure of which is incorporated by reference herein in its entirety.

CROSS-REFERENCES TO RELATED APPLICATIONS

Not applicable.

BACKGROUND OF THE INVENTION

1. Field of the Invention

The present invention relates to a device and a method for testing a solar panel, and more particularly, to a sound wave testing device and a method for testing a solar panel.

2. Descriptions of the Related Art

Various defects may be generated during the manufacturing process of solar panels, for example, diffusion of silicon materials, passivation, cracks, and pollutants, sintering defects or the like. These defects not only reduce the conversion efficiency of the solar panels, but also cause potential risks with future use. Therefore, the inspection of the defects becomes very important for the quality control of the solar panels. Currently, the inspection of the defects of solar panels mainly relies on visual inspection. However, visual inspection is only able to only detect gross cracks but is unable to detect other types of defects such as fine cracks.

Subsequent damage can be avoided if solar panels with such fine cracks can be detected and discarded as early as possible in the manufacturing process. Fine cracks, though they won't initially cause a fracture in the solar panels, they might gradually enlarge during subsequent manufacturing procedures when the solar panels are usually exposed to high mechanical loads, thus causing a fracture in the solar panels. Therefore, discarding the solar panels with fine cracks during the initial stage of the manufacturing process will help to improve the economic effectiveness of the subsequent manufacturing process.

A lot of methods for identifying fine cracks in solar panels have been proposed in the prior art, for example, the manual testing method and methods using ultrasonic waves or infrared rays. According to the manual testing method, a solar panel is swung just like a fan, and if an abnormal sound is produced, the solar panel is defective. However, this manual testing method suffers from considerable errors because it is not supported by accurate data. When ultrasonic waves are used, mechanical stress may cause fractures in the solar panel. Furthermore, although using infrared rays can test for cracks in solar panels and elements more effectively, it tests for cracks by virtue of a temperature difference; hence, it will also fail in case of defects that will not present a temperature difference.

On the other hand, there is also a testing method that can effectively test for various defects of a solar panel through the electroluminescence (EL) of the solar panel. However, defects found by this testing method may also indicate an uneven thickness of the solar panel in addition to the existence of cracks, so it cannot be specially used for the testing of cracks. Moreover, as restricted by the optical lens, this testing method cannot capture the image of an object that is 2 meters wide from a distance of less than 1 meter; however, the transferred heights of solar panel production lines are generally no greater than 1.3 m and, are usually mostly around 1 meter. Therefore, to inspect the defects of the solar panels in the production lines, a plurality of cameras with high magnification factors must be used to capture images and then the images are combined together for inspection. Although this testing method is simple, the hardware cost thereof is disproportionally high due to the high price of infrared cameras with high magnification factors, and this has hindered the widespread use of this testing method.

Accordingly, an urgent need exists in the art to provide a testing device that is simple to operate, has a low hardware cost and can prevent damage to the solar panels during the testing process.

SUMMARY OF THE INVENTION

An objective of the present invention is to provide a sound wave testing device and a method for testing a solar panel, which can determine whether a defect exists in the solar panel by measuring a sound wave transmitted through the solar panel.

Another objective of the present invention is to provide a sound wave testing device and a method for testing a solar panel, which can avoid damage to polycrystalline structures inside the solar panel to reduce the testing cost and improve the product yield.

To achieve the aforesaid objectives, a sound wave testing device for testing a solar panel according to the present invention comprises the following: at least one sound output unit for providing at least one first sound signal; at least one sound-collecting element that is disposed above the at least one sound output unit; at least one sound-receiving unit that is disposed at one end of the at least one sound-collecting element opposite the at least one sound output unit; and an isolating element that is disposed between the sound output unit and the at least one sound-collecting element; the solar panel is adapted to be disposed on the isolating element. The at least one first sound signal is transformed into at least one second sound signal while passing through the solar panel. The at least one second sound signal is then received by the at least one sound-collecting element and transmitted to the at least one sound-receiving unit. The at least one second sound signal is then transformed by the at least one sound-receiving unit into at least one digital signal for output.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

A sound wave testing device for testing a solar panel according to the present invention comprises at least one sound output unit, at least one sound-collecting element, at least one sound-receiving unit and an isolating element. The at least one sound output unit is adapted to provide at least one first sound signal; the at least one sound-collecting element is disposed above the at least one sound output unit; the at sound-receiving unit is disposed at the other end of the at least one sound-collecting element opposite the at least one sound output unit; and the isolating element is disposed between the at least one sound output unit and the at least one sound-collecting element. Additionally, the solar panel undergoing testing is adapted to be disposed on the isolating element to prevent damage to the solar panel during the testing process.

Figure 1:
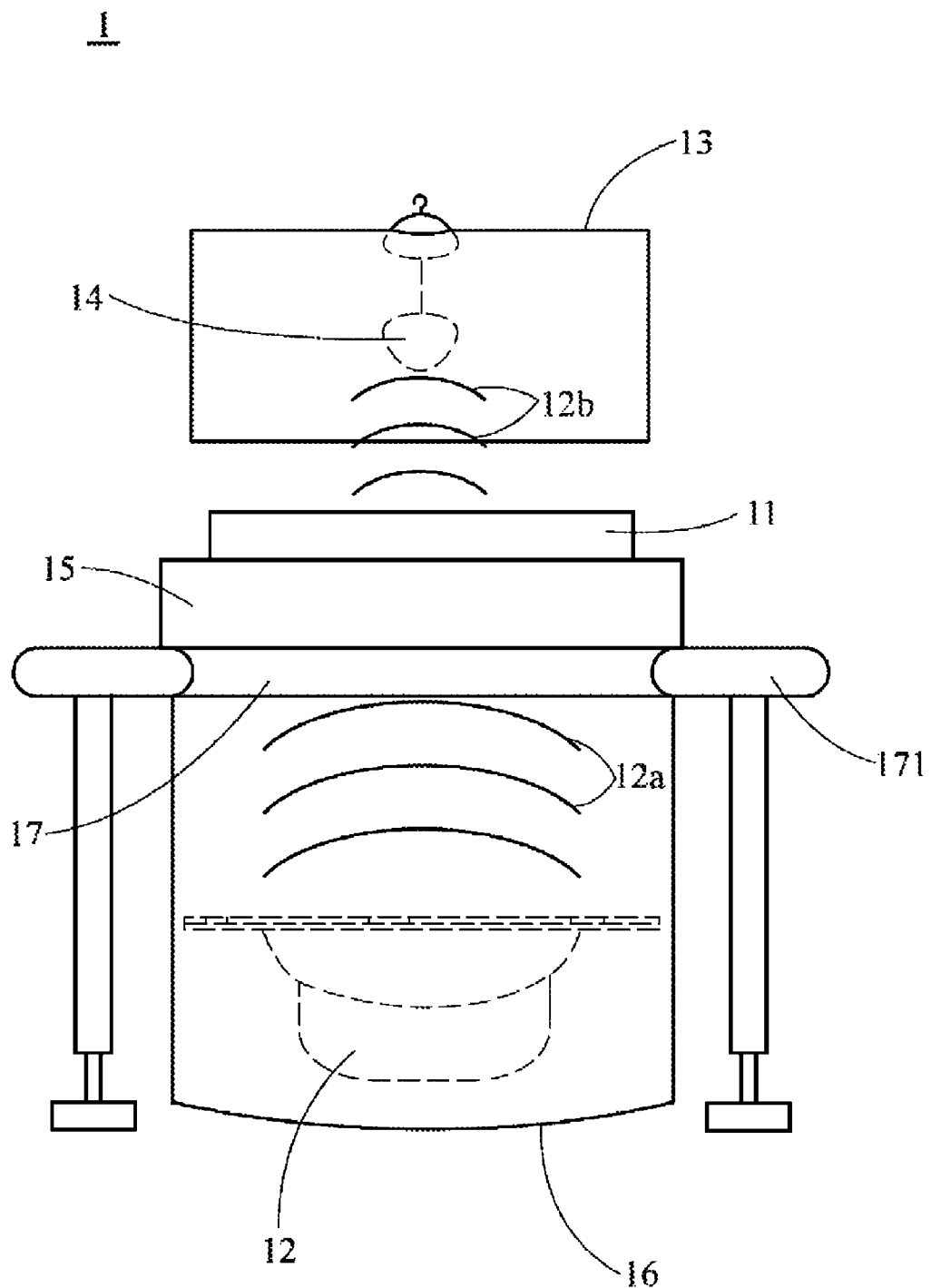
FIG. 1 is a front view of a sound wave testing device according to a first embodiment of the present invention.
Figure 2:
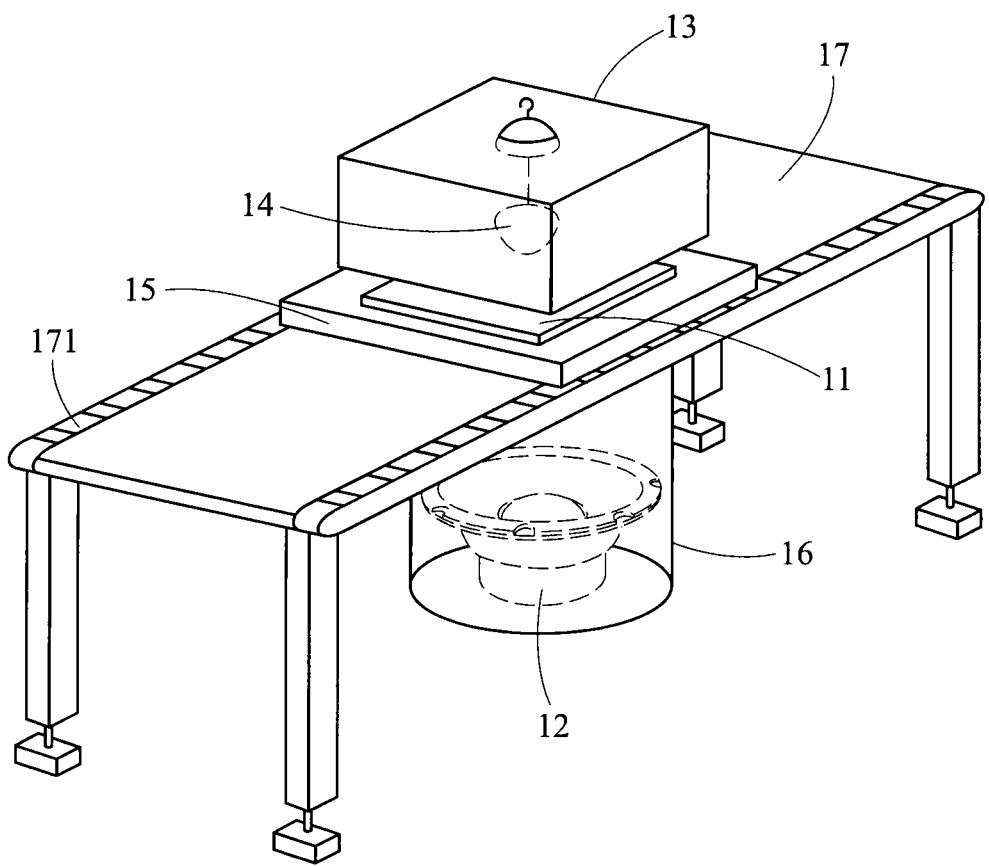
FIG. 2 is a schematic perspective view of the sound wave testing device according to the first embodiment of the present invention.

FIGS. 1 and 2 show a first embodiment of the present invention. As shown therein, the sound wave testing device 1 comprises a sound output unit 12, a sound-collecting element 13, a sound-receiving unit 14 disposed opposite the sound-collecting element 13 and an isolating element 15. A solar panel 11 is adapted to be disposed on the isolating element 15 to prevent damage to the solar panel 11 during the testing process. In this embodiment, the sound wave testing device 1 further comprises a sound absorbing element 16 and a transporting element 17. The sound absorbing element 16 is disposed around the sound output unit 12. The transporting element 17 preferably has two conveyors 171 disposed in parallel to support the isolating element 15 and the solar panel 11 disposed on the isolating element 15 and to transport them to a testing position between the sound output unit 12 and the sound-collecting element 13.

Because the sound output unit 12 provides a first sound signal 12a transmitted towards the solar panel 11, the sound absorbing element 16 is disposed around the transmitted direction of the first sound signal 12a, and the first sound signal 12a can be transmitted to the solar panel 11 totally without loss. Then, the first sound signal 12a is transformed into a second sound signal 12b when propagating into the solar panel 11. The second sound signal 12b is then received by the sound-collecting element 13 and transmitted to the sound-receiving element 14 where it is transformed into a digital signal for output.

It shall be appreciated that in the preferred implementation of the present invention, the sound output unit 12 may be a speaker, the sound-collecting element 13 may be a square mask, and the sound-receiving unit 14 may be a microphone. An area covered by the square mask (i.e., the sound-collecting element 13) is larger than or equal to an area of the solar panel 11, so that the solar panel 11 can be covered completely by the square mask. In other implementations, the sound-collecting element 13 may also be of other forms (e.g., a semi-circular form) or there may be a different number of sound-collecting elements 13; in this case, the second sound signal 12b can also be collected by the sound-collecting element 13 as long as the area covered by the sound-collecting element 13 is greater than or equal to the area of the solar panel 11. Furthermore, the space between the two conveyors 171 is empty as shown, so only the two side edges of the isolating element 15 come into contact with the two conveyors 171 in the process of transporting the solar panel 11 to the testing position. This can reduce the sheltering or reflecting effect that might possibly occur during the transmission of the first sound signal 12a. On the other hand, in addition to the functions of supporting and protecting the solar panel 11, the isolating element 15 shall further have functions of permitting the transmission of the first sound signal 12a therethrough and reducing the reflections and interferences of the sound wave; therefore, the isolating element 15 is preferably a sponge.

After the sound-receiving unit 14 has transformed the received second sound signal 12b into a digital signal, the digital signal is outputted for comparison with a standard signal in terms of frequency responses to determine the yield of the solar panel 11 and to determine whether there is a crack in the solar panel 11. It shall be particularly appreciated that the standard signal is obtained by using the sound wave testing device 1 to test a non-defective solar panel, so the yield of the solar panel 11 can be readily determined by those skilled in the art without having to compare other environmental condition parameters in the process of comparing the digital signal with the standard signal.

Figure 3A:
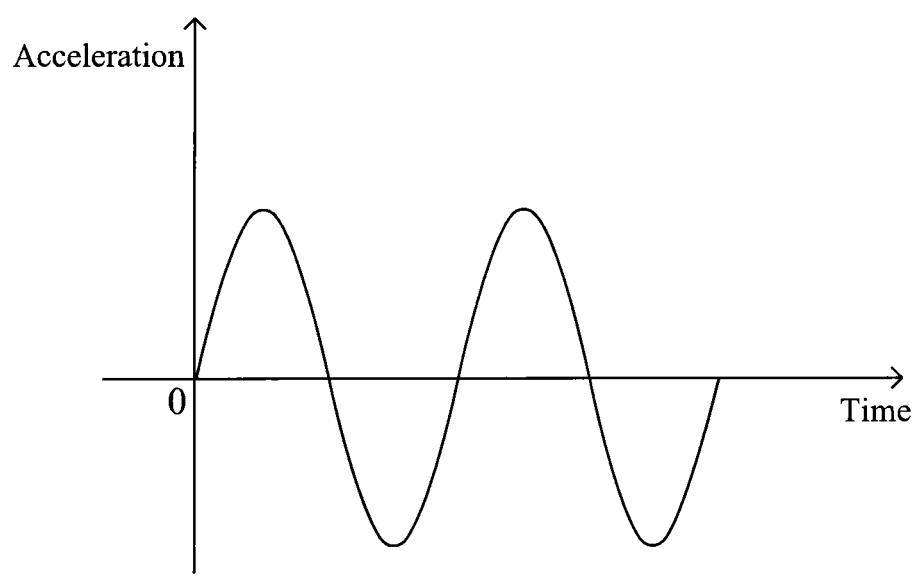
FIG. 3A is a schematic view illustrating a vibration signal of a non-defective solar panel according to the first embodiment of the present invention.
Figure 3B:
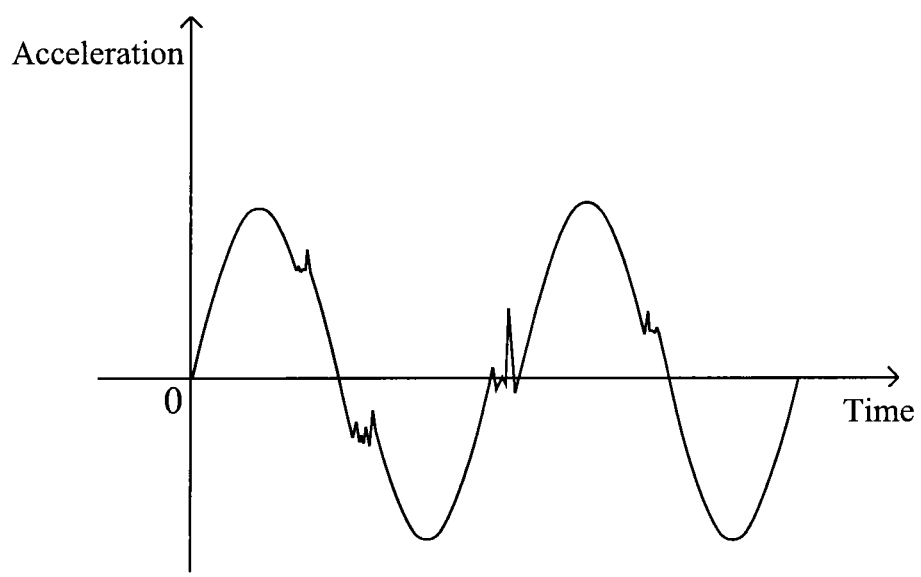
FIG. 3B is a schematic view illustrating a vibration signal of a defective solar panel according to the first embodiment of the present invention.

In this embodiment, according to a digital signal generated when the first sound signal 12a is transmitted to a non-defective solar panel, a sinusoidal waveform as shown in FIG. 3A can be drawn by the operator for use as a basis in subsequent sound wave testing. For example, if a waveform substantially coinciding with that of FIG. 3A is obtained when the first sound signal 12a is transmitted to a solar panel 11 under testing and transformed into a digital signal, then the solar panel 11 is determined to be a non-defective solar panel. Otherwise, if significant noises are found near the peaks and valleys of the waveform (i.e., the waveform is unsmooth) obtained in the sound wave test as shown in FIG. 3B, then it can be determined that the solar panel 11 is defective or that there is a cracks in the solar panel 11. It shall be appreciated that because the digital signals obtained from solar panels of different sizes, specifications or materials in the sound wave test are different from each other, the resulting waveforms will also vary from each other; therefore, apart from the aforesaid sinusoidal waveforms, waveforms of random forms may also be obtained. In this sense, the waveforms depicted in FIGS. 3A and 3B are only provided as examples but are not intended to limit the scope of the present invention.

Figure 4:
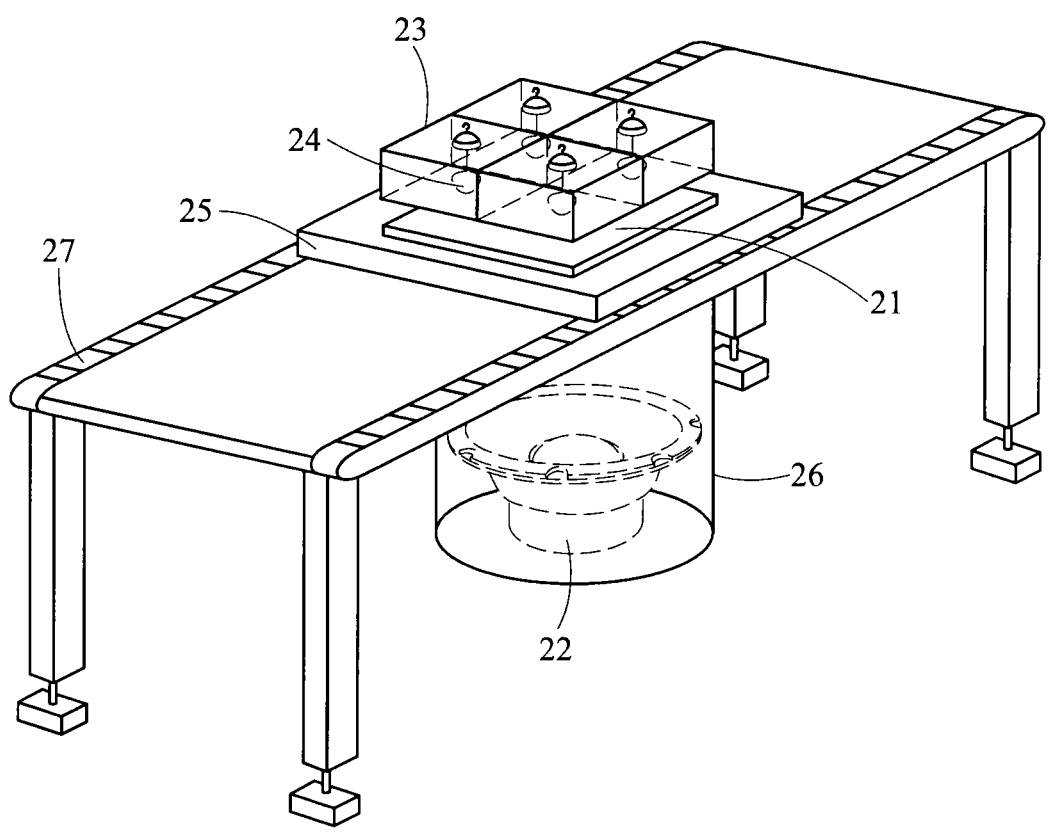
FIG. 4 is a schematic perspective view of a sound wave testing device according to a second embodiment of the present invention.

FIG. 4 is a second embodiment of the present invention. As shown, a sound wave testing device 2 of the second embodiment has a sound output unit 22, four sound-collecting elements 23, four sound-receiving units 24, an isolating element 25, a sound absorbing element 26 and a transporting element 27, all of which are substantially the same as those of the first embodiment. However, the sound wave testing device 2 of the second embodiment differs from the first embodiment mainly in that the four sound-collecting elements 23 and four sound-receiving units 24 corresponding to the sound-collecting elements 23 are disposed in the sound wave testing device 2. In other words, each of the sound-collecting elements 23 is used in combination with a sound-receiving unit 24.

Correspondingly, the solar panel 21 undergoing testing in the second embodiment is divided into four testing regions (not shown) corresponding to the array of the sound-collecting elements 23. Thus, when the first sound signal (not shown) transmitted by the sound output unit 22 is transmitted through the solar panel 21, four second sound signals (not shown) will be generated correspondingly. The second sound signals are received by the sound-collecting elements 23 and transmitted to the corresponding sound-receiving units 24 respectively, and are then transformed into four digital signals (not shown) for output. Finally, the frequency responses of the digital signals are compared with that of a standard signal to determine the yield of each testing region of the solar panel 21 and to determine whether there is a crack in each testing region of the solar panel 21.

Figure 5:
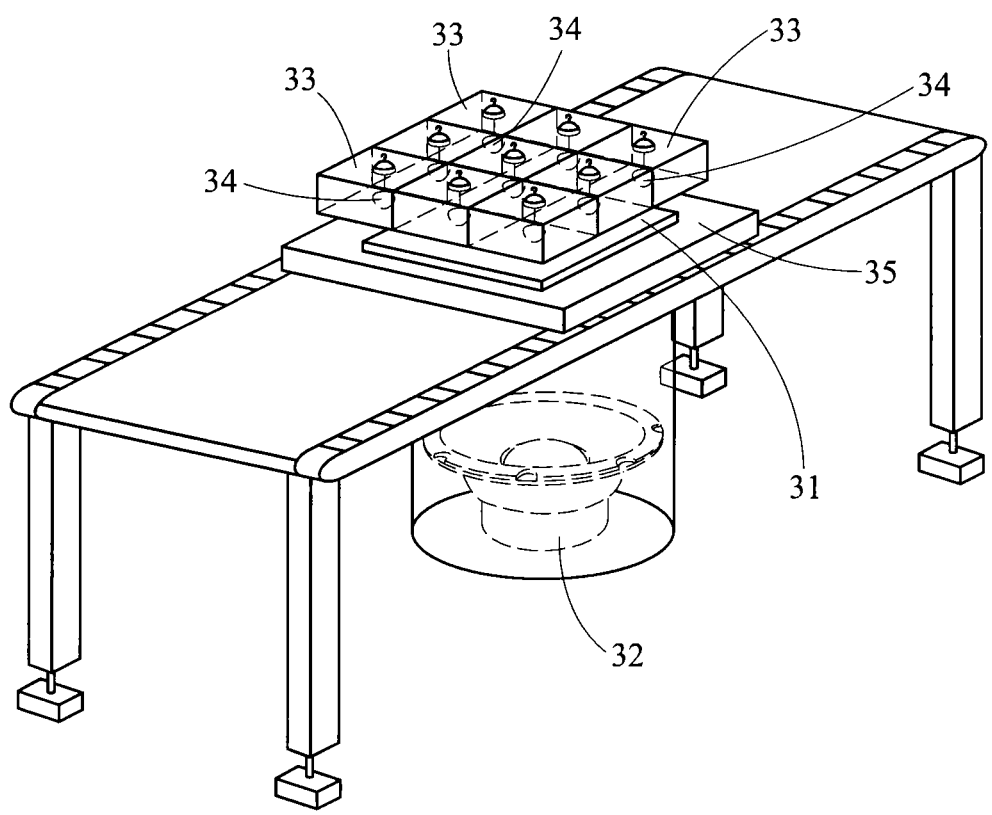
FIG. 5 is a schematic perspective view of a sound wave testing device according to a third embodiment of the present invention.

It shall be appreciated that the plurality of sound-collecting elements arranged in an array may also be disposed in other manners. As shown in FIG. 5, a third embodiment of the present invention is shown therein. The sound wave testing device 3 may also be provided with nine sound-collecting elements 33 and nine corresponding sound-receiving units 34 as long as a total area covered by the sound-collecting elements 33 is greater than or equal to the area of the solar panel 31. The solar panel 31 undergoing testing of the third embodiment is also divided into nine testing regions (not shown) corresponding to the array of the sound-collecting elements 33. Thus, when the first sound signal (not shown) transmitted by the sound output unit 32 is transmitted through the solar panel 31, nine second sound signals (not shown) will be generated correspondingly. The second sound signals are received by the sound-collecting elements 33 and transmitted to the corresponding sound-receiving units 34 respectively, and are then transformed into nine digital signals (not shown) for output. Finally, the frequency responses of the digital signals are compared with that of a standard signal to determine the yield of each testing region of the solar panel 31, to determine whether there is a crack in each test region of the solar panel 31, and to further determine the location and length of the crack.

Figure 6:
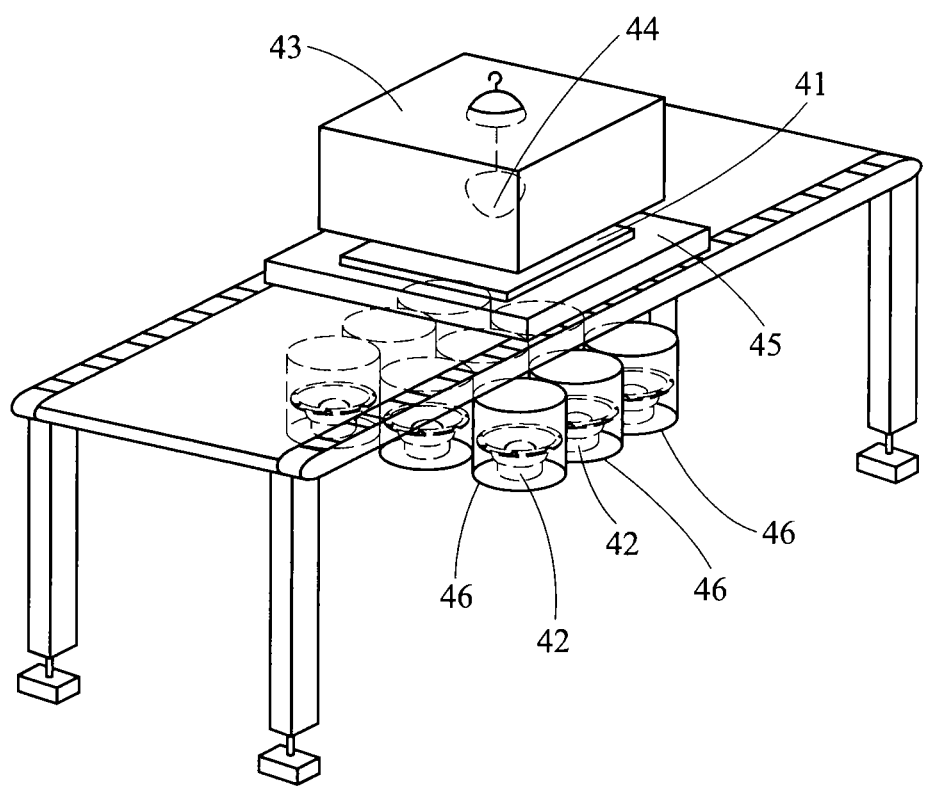
FIG. 6 is a schematic perspective view of a sound wave testing device according to a fourth embodiment of the present invention.

Similarly, other similar implementations may also be devised by those skilled in the art. In a fourth embodiment as shown in FIG. 6, the sound wave testing device 4 may also be provided with nine sound output units 42 and nine sound absorbing elements 46. The solar panel 41 may also be divided into nine testing regions (not shown), and the testing regions may be disposed in the form of a nine-square grid corresponding to the array of the sound output units 42. Then, when the nine first sound signals (not shown) transmitted by the nine sound output units 42 are transmitted through the solar panel 41, nine second sound signals (not shown) will be generated correspondingly. The second sound signals are received by the single sound-collecting element 43 and transmitted to the single corresponding sound-receiving unit 44, and are then transmitted into nine digital signals (not shown) for output. Then, frequency responses of the nine digital signals are compared with a standard signal to determine the yield of each testing region of the solar panel 41, to determine whether there is a crack in each testing region of the solar panel 41 and to further determine the location and length of the crack.

Figure 7:
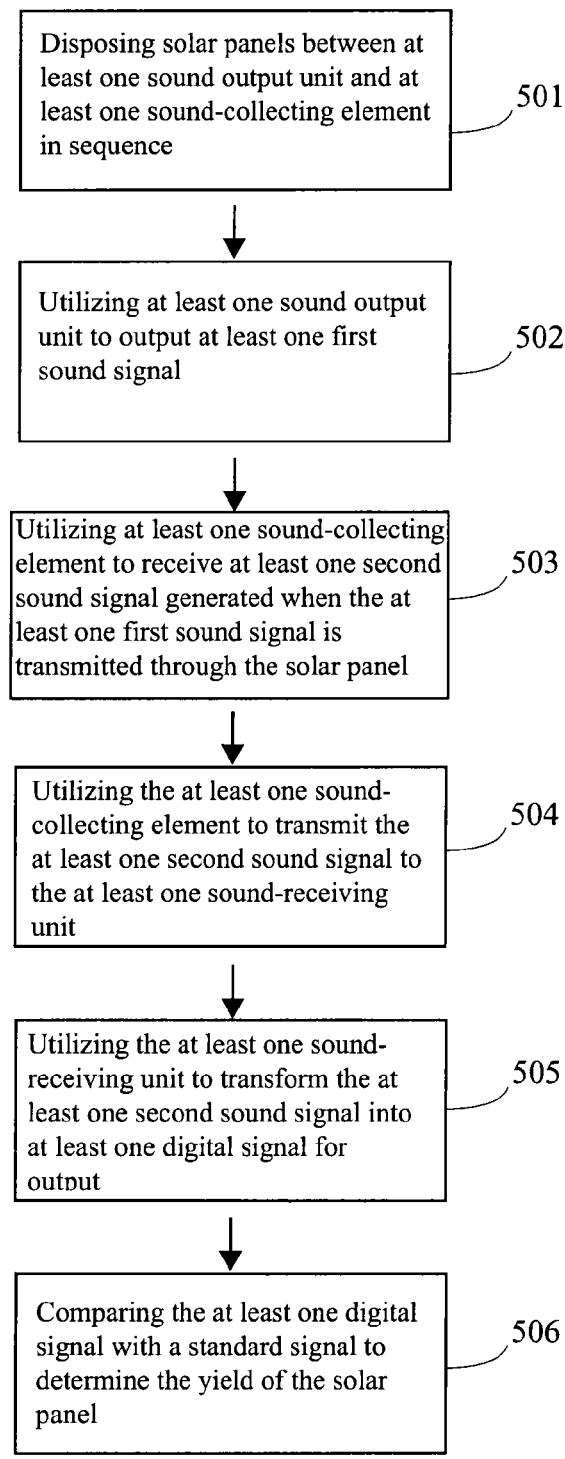
FIG. 7 is a flowchart diagram of a sound wave testing method according to the present invention.

As shown in FIG. 7, a method for testing a solar panel is also disclosed in the present invention. First, as shown in step 501, a plurality of solar panels is disposed between at least one sound output unit and at least one sound-collecting element in sequence. Then, as shown in step 502, at least one sound output unit is utilized to output at least one first sound signal. As shown in step 503, at least one second sound signal is generated when the at least one first sound signal is transmitted through the solar panel. The at least one second sound signal is received by at least one sound-collecting element. Then, as shown in step 504, the at least one second sound signal is transmitted by the at least one sound-collecting element to the at least one sound-receiving unit. Finally, as shown in step 505, the at least one second sound signal is transformed by the at least one sound-receiving unit into at least one digital signal for output, and as shown in step 506, the at least one digital signal is outputted for comparison with a standard signal in terms of the frequency response to determine the yield of the solar panel. Additionally, although step 501 only discloses the solar panels that are disposed between the at least one sound output unit and the at least one sound-collecting element, a transporting element may also be used to transport the solar panels undergoing testing between the at least one sound output unit and the at least one sound-collecting element in sequence to perform the testing operations continuously and quickly.

Because each of the solar panels is divided into a plurality of testing regions arranged in the form of an array, the sound-receiving element is adapted to receive second sound signals transmitted by the testing regions located at the front-end portion, middle portion and back-end portion of the solar panel respectively when the transporting element is used to transport the solar panel. The second sound signals are transformed by the sound-receiving unit into a plurality of digital signals for output, and then the frequency responses of the digital signals are compared with that of a standard signal to determine the yield of each of the front-end portion, the middle portion and the back-end portion, to determine whether there is a crack in each testing region of the solar panel, and to further determine the location and length of the crack. If any of the front-end portion, the middle portion or the back-end portion of the solar panel is determined to be defective or having a crack through comparison with the standard signal, the user can locally remove the defective region before subsequent processing is performed.

Other similar implementations may also be devised by those skilled in the art according to the first embodiment and the second embodiment. For example, the solar panel may be a solar panel module, and the number of the sound output units may be increased (e.g., nine sound output units as shown in FIG. 6) to provide a plurality of first sound signals. Each of the sound output units is adapted to work in combination with a corresponding sound-receiving element to transmit the first sound signal to a corresponding testing region of the solar panel; meanwhile, the sound output units may also be used in combination with a plurality of sound-collecting units and a plurality of sound-receiving units corresponding to the sound-collecting elements. In other words, the numbers of the sound output units, the sound-collecting elements and the sound-receiving units are not limited by the first embodiment and the second embodiment described above, but may be adjusted as desired.

According to the above descriptions, the device and the method for testing a solar panel according to the present invention can determine the yield of the solar panel in a simple way without the need of complex instruments or procedures and without damage to the body of the solar panel. Meanwhile, the testing results will not be affected even when the solar panel undergoing testing has a polycrystalline structure, so the sound wave testing device of the present invention helps to reduce the testing cost and improve the yield of the solar panel.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A sound wave testing device for testing a solar panel, comprising:
   at least one sound output unit, providing at least one first sound signal;
   at least one sound-collecting element, being disposed above the at least one sound output unit;
   at least one sound-receiving unit, being disposed at an end of the at least one sound-collecting element opposite the at least one sound output unit; and
   an isolating element, being disposed between the at least one sound output unit and the at least one sound-collecting element, and the solar panel is disposed on the isolating element;
   wherein the at least one first sound signal is transformed into at least one second sound signal while passing through the solar panel, the at least one second sound signal is then received by the at least one sound-collecting element and transmitted to the at least one sound-receiving unit, and the at least one second sound signal is then transformed by the at least one sound-receiving unit into at least one digital signal for output.

2. The sound wave testing device of claim 1, further comprising a transporting element for holding and transporting the isolating element and the solar panel to a testing position between the at least one sound output unit and the at least one sound-collecting element.

3. The sound wave testing device of claim 2, wherein the transporting element has two conveyors disposed in parallel for together holding the isolating element.

4. The sound wave testing device of claim 1, wherein the at least one sound-collecting element is a plurality of sound-collecting elements arranged in an array form.

5. The sound wave testing device of claim 4, wherein the at least one sound-receiving unit is a plurality of sound-receiving units arranged in an array form corresponding to the plurality of sound-collecting elements.

6. The sound wave testing device of claim 5, wherein the at least one sound output unit is one sound output unit.

7. The sound wave testing device of claim 1, wherein the isolating element is a sponge.

8. The sound wave testing device of claim 1, further comprising a sound absorbing element disposed around the propagation direction of the at least one first sound signal.

9. A method for testing a solar panel, comprising the following steps:
   (a) disposing the solar panel between at least one sound output unit and at least one sound-collecting element;
   (b) utilizing the at least one sound output unit to output at least one first sound signal;
   (c) utilizing the at least one sound-collecting element to receive at least one second sound signal generated when the at least one first sound signal passes through the solar panel;
   (d) utilizing the at least one sound-collecting element to transmit the at least one second signal to at least one sound-receiving unit; and
   (e) utilizing the at least one sound-receiving unit to transform the at least one second sound signal into at least one digital signal for output.

10. The method of claim 9, further comprising the following steps:
    (f) outputting the at least one digital signal for comparison with a standard signal so as to determine the yield of the solar panel.

11. The method of claim 9, wherein the step (a) further comprises:
    utilizing a transporting element to transport the solar panel to a position between the at least one sound output unit and the at least one sound-collecting element in sequence.

* * * * *